(12) United States Patent
Bartholomaeus et al.

(10) Patent No.: US 7,410,965 B2
(45) Date of Patent: Aug. 12, 2008

(54) DELAYED RELEASE PHARMACEUTICAL COMPOSITION CONTAINING 1-DIMETHYL-AMINO-3-(3-METHOXY PHENYL)-2-METHYL-PENTAN-3-OL

(75) Inventors: Johannes Bartholomaeus, Aachen (DE); Iris Ziegler, Rott-Roetgen (DE)

(73) Assignee: Gruenenthal GmbH, Aachen (DE)

( * ) Notice: Subject to any disclaimer, the term of this patent is extended or adjusted under 35 U.S.C. 154(b) by 457 days.

(21) Appl. No.: 10/998,159

(22) Filed: Nov. 29, 2004

(65) Prior Publication Data

US 2005/0136110 A1    Jun. 23, 2005

Related U.S. Application Data

(63) Continuation of application No. PCT/EP03/05488, filed on May 26, 2003.

(30) Foreign Application Priority Data

May 29, 2002   (DE) ................. 102 24 108

(51) Int. Cl.
| | |
|---|---|
| A61K 31/535 | (2006.01) |
| C07C 69/96 | (2006.01) |
| C07C 229/00 | (2006.01) |
| C07C 261/00 | (2006.01) |
| C07F 9/02 | (2006.01) |

(52) U.S. Cl. .................. 514/231.8; 558/190; 558/237; 560/32; 560/37

(58) Field of Classification Search ............. 514/231.8, 514/114, 452; 424/461, 468, 480, 495; 558/273, 558/190; 560/32, 37
See application file for complete search history.

(56) References Cited

U.S. PATENT DOCUMENTS

| | | | |
|---|---|---|---|
| 4,389,393 A | 6/1983 | Schor | |
| 4,728,513 A | 3/1988 | Ventouras | |
| 6,248,737 B1 | 6/2001 | Buschmann | |

FOREIGN PATENT DOCUMENTS

| | | |
|---|---|---|
| DE | 3309516 | 12/1983 |
| DE | 3625458 | 2/1987 |
| EP | 0642788 | 3/1995 |
| EP | 0693475 | 1/1996 |
| WO | WO 02/43715 | 6/2002 |
| WO | WO 03/024444 | 3/2003 |

*Primary Examiner*—Maryam Monshipouri
(74) *Attorney, Agent, or Firm*—Crowell & Moring LLP

(57) ABSTRACT

A delayed release pharmaceutical formulation containing 1-dimethylamino-3-(3-methoxyphenyl)-2-methylpentan-3-ol or a pharmaceutically acceptable salt thereof in a matrix; said matrix containing from 1 to 80 wt. % of at least one pharmaceutically acceptable, matrix-forming, hydrophilic or hydrophobic polymer and having the following in vitro dissolution rate relative to 100 wt. % of the 1-dimethylamino-3-(3-methoxyphenyl)-2-methylpentan-3-ol contained in the formulation: 3-35 wt. % released after 0.5 hour, 5-50 wt. % released after 1 hour, 10-75 wt. % released after 2 hours, 15-82 wt. % released after 3 hours, 30-97 wt. % released after 6 hours, more than 50 wt. % released after 12 hours, more than 70 wt. % released after 18 hours, and more than 80 wt. % released after 24 hours.

33 Claims, No Drawings

DELAYED RELEASE PHARMACEUTICAL COMPOSITION CONTAINING 1-DIMETHYL-AMINO-3-(3-METHOXYPHENYL)-2-METHYL-PENTAN-3-OL

CROSS REFERENCE TO RELATED APPLICATIONS

This application is a continuation of international patent application no. PCT/EP03/05488, filed May 26, 2003, designating the United States of America, and published in German as WO 03/099267 on Dec. 4, 2003, the entire disclosure of which is incorporated herein by reference. Priority is claimed based on Federal Republic of Germany patent application no. DE 102 24 108.2, filed May 29, 2002.

BACKGROUND OF THE INVENTION

The present invention relates to a pharmaceutical formulation with delayed active ingredient release that contains 1-dimethylamino-3-(3-methoxyphenyl)-2-methylpentan-3-ol or one of its pharmaceutically acceptable salts in a matrix.

1-dimethylamino-3-(3-methoxyphenyl)-2-methylpentan-3-ol is known from U.S. Pat. No. 6,248,737 (=EP 693,475), the entire disclosure of which is incorporated by reference, as an analgesically active medicament and may be administered orally. The usual formulations for oral administration of 1-dimethylamino-3-(3-methoxyphenyl)-2-methylpentan-3-ol lead to a rapid release of the active ingredient in the gastrointestinal tract, resulting in a rapid onset of the analgesic effect. At the same time it is observed that the effect rapidly wears off. Accordingly the treatment of severe chronic pain using 1-dimethylamino-3-(3-methoxyphenyl)-2-methylpentan-3-ol has hitherto required the medicament to be administered at relatively short intervals, for example 4 to 6 times a day, in order thereby to ensure a sufficient concentration of active ingredient in the patient's blood plasma. The necessity of a frequent dosage easily leads however to mistakes in administration of the medicament as well as to undesired plasma concentration fluctuations, which has a deleterious effect as regards patient compliance and therapeutic usefulness, especially in the treatment of chronic pain conditions. A pharmaceutical application form with delayed release (retard formulation) for oral administration of the active ingredient 1-dimethylamino-3-(3-methoxyphenyl)-2-methylpentan-3-ol is therefore desirable.

In the prior art, retard formulations are generally known for a large number of various active ingredients. Conventional retard forms include, inter alia, coated retard forms and matrix retard forms.

In coated retard forms such as those described, for example, in U.S. Pat. No. 4,728,513 (=DE 36 25 458), the core of a pharmaceutical composition containing an active ingredient is provided with a coating of one or more hydrophilic and/or hydrophobic polymers that delays the release of the active ingredient.

In matrix retard forms, the active ingredient is contained in a matrix formed from one or more carrier materials, which controls the release of the active ingredient. Thus for example, U.S. Pat. No. 4,389,393 (=DE 33 09 516) discloses a process for the production of matrix formulations with hydroxypropylmethyl-cellulose (HPMC) as carrier material and to some extent a delayed release of the active ingredient, wherein the active material does not comprise more than one third of the weight of the formulation and consists of at least one hydroxypropylmethylcellulose that has a methoxy content of 16-24 wt. %, an hydroxypropyl content of 4-32 wt. % and a number average molecular weight of at least 50,000. The formulations disclosed in U.S. Pat. No. 4,389,393 contain HPMCs with viscosities (in 2 wt. % aqueous solution at 20° C.) between 15 and 30,000 cPs (15 to 30,000 mPa·s). A release behavior independent of the pH value of the dissolution medium is not disclosed in U.S. Pat. No. 4,389,393.

SUMMARY OF THE INVENTION

An object of the present invention is accordingly to provide a pharmaceutical formulation with delayed active ingredient release containing 1-dimethylamino-3-(3-methoxyphenyl)-2-methylpentan-3-ol.

This object is achieved by a pharmaceutical formulation with delayed release that contains 1-dimethylamino-3-(3-methoxyphenyl)-2-methylpentan-3-ol or a pharmaceutically acceptable salt thereof in a matrix with delayed release of active ingredient, wherein the matrix contains 1 to 80 wt. %, preferably 5 to 80 wt. %, of one or more hydrophilic or hydrophobic polymers as pharmaceutically acceptable matrix-forming agents, and has the following in vitro release rate measured using the Ph. Eur. paddle method at 75 rpm in a buffer (according to Ph. Eur.) at a pH value of 6.8 at 37° C. and with UV spectrometric detection:

3-35 wt. % of 1-dimethylamino-3-(3-methoxyphenyl)-2-methylpentan-3-ol (referred to 100 wt. % of active ingredient) released after 0.5 hour, 5-50 wt. % of 1-dimethylamino-3-(3-methoxyphenyl)-2-methylpentan-3-ol released after 1 hour 10-75 wt. % of 1-dimethylamino-3-(3-methoxyphenyl)-2-methylpentan-3-ol released after 2 hours 15-82 wt. % of 1-dimethylamino-3-(3-methoxyphenyl)-2-methylpentan-3-ol released after 3 hours 30-97 wt. % of 1-dimethylamino-3-(3-methoxyphenyl)-2-methylpentan-3-ol released after 6 hours more than 50 wt. % of 1-dimethylamino-3-(3-methoxyphenyl)-2-methylpentan-3-ol released after 12 hours, more than 70 wt. % of 1-dimethylamino-3-(3-methoxyphenyl)-2-methylpentan-3-ol released after 18 hours, and more than 80 wt. % of 1-dimethylamino-3-(3-methoxyphenyl)-2-methylpentan-3-ol released after 24 hours.

It has surprisingly been found that the formulation according to the invention provides for the delayed release of the active ingredient 1-dimethylamino-3-(3-methoxyphenyl)-2-methylpentan-3-ol when administered orally and is thus suitable for administration at intervals of at least 12 hours. The formulation according to the invention accordingly provides a treatment for pain as well as a treatment for increased urinary urgency or urinary incontinence, in particular urgency incontinence and stress incontinence, in connection with which 1-dimethylamino-3-(3-methoxyphenyl)-2-methylpentan-3-ol need be administered only once daily, for example at intervals of 24 hours, or twice daily, for example at intervals of 12 hours, in order to ensure a sufficient plasma concentration of the active ingredient. A corresponding effect duration and the maintenance of a sufficient blood plasma level is confirmed by simulation studies and experimental investigations.

It is particularly surprising in this connection that the formulation according to the invention not only assures, due to the delayed release, a long-lasting therapeutic effectiveness over a relatively long period (at least 12 hours), but at the same time on first administration of the medicament permits a rapid build up of the active ingredient in the plasma, which leads to a rapid pain relief in the patient (rapid onset effect). Thus, upon administration of the formulation according to the invention to a patient suffering pain, the pain can be rapidly alleviated without the analgesic effect also rapidly attenuating. The formulation according to the invention thus combines properties of a formulation with immediate release of active ingredient—rapid relief of pain due to sufficiently high active substance concentration shortly after administration of the medicament—with properties of a formulation with delayed release—long-lasting analgesic effect on account of a sufficiently high active ingredient level over a prolonged time. The patient suffering from pain can thus effectively alleviate his/her pain by taking the analgesic in the formulation according to the invention and at the same time can, without further measures and simply by regular administration of the medicament at intervals of 12 (or 24) hours, effectively relieve the pain for a relatively long period.

It is also advantageous that, due to the constant and sufficiently high active ingredient level of the 1-dimethylamino-3-(3-methoxyphenyl)-2-methylpentan-3-ol compound over a fairly long time that is achieved by the formulations and at the same time without further measures and simply by administration at intervals of 12 (or 24) hours, it is possible effectively to treat, alleviate or relieve over a relatively long time increased urinary urgency or urinary incontinence, in particular urgency incontinence and stress incontinence.

The active ingredient of the formulation according to the invention is contained in a matrix with delayed release. It is however also conceivable for the active ingredient to be contained in a matrix exhibiting a conventional release behaviour and to achieve the delayed release by a retard coating.

If the formulation according to the invention contains a matrix with delayed release, the matrix comprises 1-80 wt. % of one or more hydrophilic or hydrophobic polymers as pharmaceutically acceptable matrix-forming agents, for example gums, cellulose ethers, cellulose esters, acrylic resins, materials derived from proteins, fats, waxes, fatty alcohols or fatty acid esters. When using hydrophilic polymers as matrix-forming agent it is preferred that the matrix contains 5 to 80 wt. % of matrix-forming agent.

The present invention also provides a pharmaceutical formulation that contains 1-dimethylamino-3-(3-methoxyphenyl)-2-methylpentan-3-ol or a pharmaceutically acceptable salt thereof in a matrix with delayed active ingredient release, the matrix containing 1 to 80 wt. %, in particular 5 to 80 wt. %, of one or more hydrophilic or hydrophobic polymers as pharmaceutically acceptable matrix-forming agent, and which is characterised in that it comprises as pharmaceutically acceptable matrix-forming agent cellulose ethers and/or cellulose esters that have a viscosity of 3000 to 150,000 mPa·s in a 2 wt. % aqueous solution at 20° C. (The viscosity determination is carried out by means of capillary viscosimetry according to Pharm. Eu.) The compositions have the release profile according to the invention specified above.

Preferred pharmaceutically acceptable matrix-forming agents include cellulose ethers and/or cellulose esters that in a 2 wt. % aqueous solution at 20° C. have a viscosity between 10,000 mPa·s, in particular 50,000 mPa·s, and 150,000 mPa·s.

Particularly suitable pharmaceutically acceptable matrix-forming agents are selected from the group comprising hydroxypropylmethylcelluloses (HPMC), hydroxyethylcelluloses, hydroxypropylcelluloses (HPC), methylcelluloses, ethylcelluloses and carboxymethylcelluloses, and in particular are selected from the group comprising HPMCs, hydroxyethylcelluloses and HPCs. Most particularly preferred are HPMCs with a viscosity of ca. 100,000 mPa·s measured in a 2 wt. % aqueous solution at 20° C.

The active ingredient 1-dimethylamino-3-(3-methoxyphenyl)-2-methylpentan-3-ol may be present as such, i.e. as free base, but may also be present in the form of a pharmaceutically acceptable salt, for example as the hydrochloride. The preparation of the free base is known from U.S. Pat. No. 6,248,737 (=EP 693,475), the entire disclosure of which is incorporated by reference. Insofar as the preparation of pharmaceutically acceptable salts—such as the hydrochloride—is also not disclosed in U.S. Pat. No. 6,248,737, these may be obtained from the free base by methods generally known in the art.

1-dimethylamino-3-(3-methoxyphenyl)-2-methylpentan-3-ol has two asymmetric (chiral) centers, with the result that the compound may exist in the form of four different stereoisomers. In the formulation according to the invention 1-dimethylamino-3-(3-methoxyphenyl)-2-methylpentan-3-ol may be present as a mixture of all four diastereomers in an arbitrary mixture ratio, but also as a mixture of two or three of the four stereoisomers, or in the form of a pure stereoisomer. Preferred stereoisomers within the scope of the invention are (+)-(2R,3R)-1-dimethylamino-3-(3-methoxyphenyl)-2-methylpentan-3-ol and (−)-(1S,2S)-1-dimethylamino-3-(3-methoxyphenyl)-2-methylpentan-3-ol, which may be present in the formulation according to the invention as a mixture, in particular as a 1:1 mixture (racemate), or particularly preferably in the form of a pure stereoisomer. The term "active ingredient" is therefore understood for the purposes of the present invention to denote 1-dimethylamino-3-(3-methoxyphenyl)-2-methylpentan-3-ol compound as a mixture of various of its stereoisomers or as one of its pure stereoisomers, either in the form of the respective free base or in the form of a pharmaceutically acceptable salt.

The content of delayed release active ingredient in the pharmaceutical compositions according to the present invention is preferably between 0.5 and 85 wt. %. The content of pharmaceutically acceptable matrix-forming agent is preferably between 8 and 40 wt. %. Particularly preferred are formulations with a content of delayed release active ingredient of between 3 and 70 wt. %, in particular between 8 and 66 wt. %, and a content of pharmaceutically acceptable matrix-forming agent of between 10 and 35 wt. %, in particular between 10 and 30 wt. %. If the enantiomerically-pure (+)-(2R,3R)-1-dimethylamino-3-(3-methoxyphenyl)-2-methylpentan-3-ol (or a mixture of the (+) and (−) enantiomers with a large excess of the (+) enantiomer) is used as active ingredient, it is particularly preferred if the content of active ingredient is at the lower level, i.e. is between 0.5 and 25 wt. % (relative to the total weight). If the enantiomerically-pure (−)-(2S,3S)-1-dimethylamino-3-(3-methoxyphenyl)-2-methylpentan-3-ol (or a mixture of the (+) and (−) enantiomers with a large excess of the (−) enantiomer) is used as active ingredient, it is particularly preferred if the active ingredient content is between 16 and 66 wt. %.

Further constituents of the matrix of the formulation according to the invention may optionally include digestible long-chain (i.e. with 8 to 50 C atoms, preferably 12 to 40 C atoms) unsubstituted or substituted hydrocarbons, such as for example fatty alcohols, fatty acid glyceryl esters, mineral oils and vegetable oils, as well as waxes. Hydrocarbons with a melting point between 25° and 90° C. are preferred. In particular fatty alcohols are preferred, most particularly preferred being lauryl alcohol, myristyl alcohol, stearyl alcohol, cetyl alcohol and cetylstearyl alcohol. Their content in the matrix is 0 to 60 wt. %. Alternatively or in addition polyethylene glycols may also be contained in the matrix in an amount of 0 to 60 wt. %.

The pharmaceutical formulations according to the invention may in addition contain as further constituents conventional pharmaceutical auxiliary substances such as fillers, for example lactose, microcrystalline cellulose (MCC) or calcium hydrogen phosphate, as well as glidants, intestinal lubricants and flow regulating agents, for example talcum, magnesium stearate, stearic acid and/or highly dispersed silicon dioxide, whose total weight in the tablet is between 0 and 80 wt. %, preferably between 5 and 65 wt. %.

In many cases the release rate of an active ingredient from an application form depends on the pH of the release medium. This may vary in a pH range from below 1 to about 8 during passage of the medicament through the gastrointestinal tract. These variations may differ from person to person taking the medicament. Also, there may be a different pH value/time profile during passage through the gastrointestinal tract in one and the same person from one administration to the next. If the release rate of the active ingredient from the medicament depends on the pH, this can lead to different release rates in vivo and thus to different bioavailability behaviors. The release profiles of the active ingredient (in the form of the base or one of its pharmaceutically acceptable salts) from a pharmaceutical formulation according to the invention are however surprisingly independent of the pH value, such as may physiologically occur during passage through the gastrointestinal tract. The release profiles at an ambient pH value of 1.2, 4.0 and 6.8 are identical to one another and also when compared to the release during a pH value/time profile from pH 1.2 through pH 2.3 and pH 6.8 up to pH 7.2.

It has been found that to achieve delayed release of active ingredient from the formulation according to the invention, preferably present in tablet form, it is immaterial whether, under otherwise identical dimensions and identical composition of the tablet as regards the active ingredient, the matrix-forming agent and the optional constituents, a water-soluble filler, for example lactose, is used as filler, or an insoluble filler that does not swell in the aqueous medium, for example calcium hydrogen phosphate, is used as filler, or an insoluble filler that swells in aqueous medium, for example microcrystalline cellulose, is used as filler. All such formulations exhibit a release behavior corresponding to one another.

It is furthermore surprising that in the compositions according to the invention, for a given amount of active ingredient the amount of matrix-forming agent and the amount of optional constituents may in each case vary over a relatively large range without the therapeutic effectiveness of at least 12 hourly or twice daily administration being compromised (as long as the quantitative limits for active ingredient, matrix-forming agent and the further, optional constituents are maintained). An effectiveness of at least 12 hours is assured, for example, with a content of active ingredient of ca. 32.25 wt. % (relative to the total weight of the composition) in a composition comprising ca. 12.9 wt. % of HPMC with a viscosity of 100,000 mPa·s as matrix-forming agent and a content of, for example, MCC as filler of ca. 52.6 wt. %, as well as in a composition comprising ca. 25.8 wt. % of the same HPMC and ca. 39.7 wt. % of MCC (or lactose monohydrate) with otherwise the same amounts of glidant, intestinal lubricant and flow regulating agent. The same also applies to compositions according to the invention with a higher or lower content of active ingredient within the specified limits.

Also extremely surprising is the observation that when administering the pharmaceutical formulations according to the invention with delayed release of active ingredient to human experimental subjects, despite the high first-pass effect for the active ingredient an unaltered bioavailability is achieved, contrary to expectations, compared to formulations with immediate release of active ingredient.

Those compositions according to the invention are furthermore preferred whose $t_{max}$ value in the plasma concentration/time diagram in vivo is between 2 and 10 hours, in particular between 3.5 and 6 hours and most particularly preferably between 4 and 5.5 hours after oral administration of the composition, i.e. whose peak plasma level occurs in the aforementioned timeframes.

The formulation according to the invention contains the active ingredient 1-dimethylamino-3-(3-methoxyphenyl)-2-methylpentan-3-ol as such and/or as a pharmaceutically acceptable salt in an amount of normally 2.5 to 800 mg, in particular 5 to 400 mg, most particularly preferably 10 to 250 mg (weight of the active ingredient 1-dimethylamino-3-(3-methoxyphenyl)-2-methylpentan-3-ol as hydrochloride) per dosage unit, wherein the release behavior of the formulation according to the invention is not affected by the exact amount of the active ingredient as long as the quantitative limits specified above are maintained. It is preferred if the more active (+)-(2R,3R)-1-dimethylamino-3-(3-methoxyphenyl)-2-methylpentan-3-ol is present in an amount of 2.5 to 80 mg, in particular 5 to 40 mg and most particularly preferably in an amount of 10 to 25 mg of active ingredient (relative to the hydrochloride) in the formulations according to the invention, and specifically with the proviso that the quantitative limits specified above are maintained.

Within the scope of the present invention, the term "pharmaceutically acceptable (or tolerable) salts of the active ingredient" refers to salts of the active ingredient that are physiologically compatible in pharmaceutical use, in particular for use in mammals and/or humans. Such pharmaceutically acceptable salts may be formed for example with inorganic or organic acids.

The pharmaceutical formulations according to the invention may exist in the form of simple tablets as well as coated tablets, for example as film tablets or sugar-coated tablets. Usually the tablets are round and biconvex. Oblong tablet shapes that allow the tablet to be divided are also possible. Furthermore granules, spheroids, pellets or microcapsules, which may be packed in sachets or capsules or compressed into dispersible tablets, are also possible within the scope of the invention.

One or more coating layers may be used for the coated tablets. Suitable as coating materials include known hydroxypropylmethylcelluloses with a low viscosity of ca. 1 to 100 mPa·s and low molecular weight of <10,000 (e.g. Pharmacoat 606 with a viscosity of 6 mPa·s in a 2 wt. % aqueous solution at 20° C.), which only slightly affect the release profile of the medicaments according to the invention. Diffusion coatings known to the person skilled in the art, for example based on swellable but water-insoluble poly(meth)acrylates, lead to a modulation of the delay of the release of active ingredient from pharmaceutical formulations according to the invention. The tablet core containing the active ingredient and releasing the latter in a delayed manner, with an active ingredient content preferably between 0.5 and 85 wt. %, particularly preferably between 3 and 70 wt. % and most particularly preferably between 8 and 66 wt. %, may be coated by various methods known to the person skilled in the art, for example sugar coating, spraying from solutions or suspensions or by powder application methods, with additional active ingredient that is not released in a delayed manner like the initial dose, although this is not absolutely necessary for the desired delayed release with simultaneous rapid build up of the active ingredient for the rapid relief of pain on first administration of the pharmaceutical formulation according to the invention. Further modifications include multilayer tablets and laminated tablets, in which 1-dimethylamino-3-(3-methoxyphenyl)-2-methylpentan-3-ol or one of its pharmaceutically acceptable salts in one or more layers of the multilayer tablet with a content of active ingredient preferably between 0.5 and 85 wt. %, particularly preferably between 3 and 70 wt. % and most particularly preferably between 8 and 66 wt. %, and in the core of the laminated tablet with a content of active ingredient preferably between 0.5 and 85 wt. %, particularly preferably between 3 and 70 wt. % and most particularly preferably between 8 and 66 wt. %, is released in a delayed manner by a pharmaceutically acceptable matrix-forming agent, and the release of the active ingredients in one or more layers of the multilayer tablet or the outer lamination layer of the laminated tablets takes place in an unretarded manner. Multilayer tablets and laminated tablets may contain one or more coatings free of active ingredient.

Instead of a retard matrix, it is also possible to use in the pharmaceutical formulation with delayed release a normal release matrix with a coating that delays the release of the active ingredient. In this connection the active ingredient may for example be contained in a conventional matrix of microcrystalline cellulose and optionally further pharmaceutical auxiliary substances such as binders, fillers, glidants, intestinal lubricants and flow regulating agents, which are coated or covered with a material that controls the delayed release of the active ingredient in aqueous medium. Suitable coating agents include, for example, water-insoluble waxes and polymers such as polymethacrylates (Eudragit or the like) or water-insoluble celluloses, in particular ethyl cellulose. Optionally the coating material may also contain water-soluble polymers such as polyvinylpyrrolidone, water-soluble celluloses such as hydroxypropylmethylcellulose or hydroxypropylcellulose, other water-soluble agents such as Polysorbate 80, or hydrophilic pore-forming agents such as polyethylene glycol, lactose or mannitol.

The compositions according to the invention may for example be produced by the following general methods:

The constituents of the composition (active ingredient, matrix-forming agent and optional constituents) are weighed out in turn and then screened on a conventional screening machine. For example, the Quadro Comil U10 screening machine may be used for this purpose, a normal screen size being ca. 0.813 mm. The screened material is then mixed in a container mixer, for example in a Bohle container mixer, under the following typical operating conditions: duration ca. 15 minutes±45 sec. at a rotational speed of 20±1 rpm. The resulting powder mixture is then compressed into tablets in a pelletizing machine. For example, a Korsch EKO pelletizing machine with a round 10 mm diameter stamp having the contour of sugar-coated pills may be used for this purpose. Alternatively, the powder mixture may be compacted and the resulting moldings subsequently screened (Comil 3 mm friction slicing screen followed by 1.2 mm round hole screen), with the resultant granules then being compressed as described above with the addition of lubricant (e.g. magnesium stearate) on for example an EKO pelletising machine with 10 mm round stamps. The granulation may also be carried out by wet granulation based on aqueous or organic solvents. Aqueous solvents with or without suitable binders are preferred. The production process may be adapted without any difficulty to the particular requirements of a given situation and/or to the desired application form according to procedures that are well known in the art.

The pharmaceutical formulations according to the invention are characterised by a high reproducibility of the release properties of the compositions that contain 1-dimethylamino-3-(3-methoxyphenyl)-2-methylpentan-3-ol or one of its pharmaceutically acceptable salts. The release profile of the formulations according to the invention has been found to be stable over a storage time of at least one year under the conventional storage conditions according to the ICH Q1AR Stability Testing Guideline.

A single or double daily administration of a pharmaceutical formulation according to the invention to a patient assures a good therapeutic effectiveness not only in chronically severe pain but also a good therapeutic effectiveness in the treatment of increased urinary urgency or urinary incontinence, in particular stress incontinence and urgency incontinence.

Accordingly, the present invention also provides for the use of a pharmaceutical formulation according to the invention or a tablet according to the invention for treating pain, in particular chronic, visceral, neuropathic or acute pain or inflammation pain.

The invention furthermore provides for the use of 1-dimethylamino-3-(3-methoxyphenyl)-2-methylpentan-3-ol for treating pain, in particular chronic, visceral, neuropathic or acute pain or inflammation pain, in which the 1-dimethylamino-3-(3-methoxyphenyl)-2-methylpentan-3-ol is contained in a pharmaceutical formulation according to the invention.

A further object of the present invention was to provide substances or pharmaceutical formulations or medicaments that are helpful in the treatment of increased urinary urgency or urinary incontinence, and that in particular release effective doses that exhibit fewer side effects and/or analgesic effects than medicaments known from the prior art.

Urinary incontinence is the involuntary voiding of urine. This occurs in an uncontrolled manner if the pressure within the bladder exceeds the pressure that is necessary to close the ureter. Causes may include on the one hand an increased internal bladder pressure (for example due to detrusor instability) resulting in urgency incontinence, and on the other hand a reduced sphincter pressure (for example after childbirth or surgical intervention), resulting in stress incontinence. The detrusor is the collective term for the coarse bundles of multilayer muscles of the bladder wall, whose contraction leads to release of urine; the sphincter is the constrictor muscle of the urethra. Mixed forms of these types of incontinence as well as so-called overflow incontinence (e.g. in benign prostatic hyperplasia) or reflex incontinence (e.g. after spinal cord injury) occur. Further details can be found in Chutka, D. S. and Takahashi, P. Y., 1998, Drugs 550: 587-595.

Urinary urgency is the state of increased bladder muscle tension leading to voiding of urine (micturition) when the bladder is almost full (or when its capacity is exceeded). This muscle tone acts as a stimulus to pass urine. Increased urinary urgency is understood in this connection to mean in particular the occurrence of premature or more frequent and sometimes even painful urinary urgency up to so-called dysuria. This consequently leads to a significantly increased frequency of micturition. Causes may include, inter alia, inflammation of the bladder and neurogenic bladder disorders, as well as also bladder tuberculosis. However, all causes have not yet been elucidated.

Increased urinary urgency and also urinary incontinence are regarded as extremely unpleasant and there is therefore a clear need to achieve the greatest possible long-term improvement in patients affected by these medical conditions. Increased urinary urgency and in particular urinary incontinence are normally treated with substances that act on the reflexes of the lower urinary tract (Wein A. J., 1998, Urology 51 (Suppl. 21): 43-47). In general these are medicaments that have a blocking effect on the detrusor muscle, which is responsible for the internal bladder pressure. These medicaments include for example parasympatholytics such as oxybutynin, propiverine or tolterodine, tricyclic antidepressants such as imipramine, or muscle relaxants such as flavoxate. Other medicaments that in particular increase the resistance of the urethra or cervix of the bladder have similarities with α-adrenoreceptors such as ephedrine, with β-adrenoreceptors such as clenbutarol, or are hormones such as oestradiol. Also, certain opioids, diarylmethylpiperazines and diarylmethylpiperidines have been described for this medical condition in U.S. Pat. No. 5,552,404 (=WO 93/15062) the entire disclosure of which is incorporated by reference.

In the medical conditions that are of interest here, it should be noted that in general these involve the very long-term use of medicaments and, in contrast to many situations in which analgesics are used, patients suffer very unpleasant but not intolerable discomfort. Accordingly in this case—even more than with analgesics—care should be taken to avoid side effects if the patient does not wish to exchange one discomfort for another. Furthermore, in the long-term treatment of urinary incontinence analgesic effects are also largely undesirable.

Yet another object of the present invention was accordingly to find substances or pharmaceutical formulations or medicaments that are helpful in the treatment of increased urinary urgency or urinary incontinence.

It was now surprisingly found that 1-dimethylamino-3-(3-methoxyphenyl)-2-methylpentan-3-ol and in particular the pharmaceutical formulations according to the invention containing 1-dimethylamino-3-(3-methoxyphenyl)-2-methylpentan-3-ol have an outstanding effect on bladder function and accordingly are ideally suitable for treating the corresponding medical conditions.

The present invention accordingly also provides for the use of a pharmaceutical formulation according to the invention or a tablet according to the invention for producing a medicament for treating increased urinary urgency or urinary incontinence.

The invention in addition provides for the use of 1-dimethylamino-3-(3-methoxyphenyl)-2-methylpentan-3-ol for treating increased urinary urgency or urinary incontinence, in which 1-dimethylamino-3-(3-methoxyphenyl)-2-methylpentan-3-ol is contained in a pharmaceutical formulation according to the invention.

EXAMPLES

The following examples serve to illustrate the present invention and preferred embodiments, but are not intended to restrict the scope thereof.

Example 1

Matrix tablets with the following composition per tablet

| | |
|---|---|
| 1-dimethylamino-3-(3-methoxyphenyl)-2-methylpentan-3-ol; hydrochloride | 5 mg |
| Hydroxypropylmethylcellulose (Metolose 90 SH 100,000 from the Shinetsu company), 100,000 mPa · s | 80 mg |
| Microcrystalline cellulose (Avicel PH 101 from the FMC company) | 50 mg |
| Lactose monohydrate (Lactose 200 from the Meggie company) | 169 mg |
| Highly dispersed silicon dioxide | 3 mg |
| Magnesium stearate | 3 mg |
| Total amount | 310 mg | were produced in the following way in a batch size of 2000 tablets:

All constituents were weighed out and screened on a Quadro Comil U10 screening machine using a screen size of 0.813 mm, mixed in a container mixer (Bohle LM 40) for 15 minutes±15 sec. at a rotational speed of 20±1 rpm, and compressed on a Korsch EKO eccentric press into tablets with a diameter of 10 mm having the contours of sugar-coated pills, a convex radius of 8 mm and a mean tablet weight of 310 mg.

The in vitro release was measured using the Ph. Eur. paddle method at 75 rpm in 900 ml of buffer pH 6.8 according to Ph. Eur. at 37° C. and with UV spectrometric detection, and is given in the following table.

| Time [min] | Released total amount of the active ingredient [%] |
|---|---|
| 0 | 0 |
| 30 | 17 |
| 240 | 75 |
| 480 | 95 |
| 720 | 100 |

Example 2

Matrix tables with the following composition per tablet

| | |
|---|---|
| 1-dimethylamino-3-(3-methoxyphenyl)-2-methylpentan-3-ol; hydrochloride | 50 mg |
| Hydroxypropylmethylcellulose (Metolose 90 SH 100,000 from the Shinetsu company), 100,000 mPa · s | 80 mg |
| Microcrystalline cellulose (Avicel PH 101 from the FMC company) | 174 mg |
| Highly dispersed silicon dioxide | 3 mg |
| Magnesium stearate | 3 mg |
| Total amount | 310 mg | were produced in the following way in a batch size of 2000 tablets:

All constituents were weighed out and screened on a Quadro Comil U10 screening machine using a screen size of 0.813 mm, mixed in a container mixer (Bohle LM 40) for 15 minutes±15 sec. at a rotational speed of 20±1 rpm, and compressed on a Korsch EKO eccentric press into tablets with a diameter of 10 mm having the contours of sugar-coated pills, a convex radius of 8 mm and a mean tablet weight of 310 mg.

The in vitro release was measured using the Ph. Eur. paddle method at 75 rpm in 900 ml of buffer pH 6.8 according to Ph. Eur. at 37° C. and with UV spectrometric detection, and is given in the following table.

| Time [min] | Released total amount of the active ingredient [%] |
|---|---|
| 0 | 0 |
| 30 | 20 |
| 240 | 63 |
| 480 | 81 |
| 720 | 91 |

Example 3

Matrix tables with the following composition per tablet

| | |
|---|---|
| 1-dimethylamino-3-(3-methoxyphenyl)-2-methylpentan-3-ol; hydrochloride | 100 mg |
| Hydroxypropylmethylcellulose (Metolose 90 SH 100,000 from the Shinetsu company), 100,000 mPa·s | 80 mg |
| Microcrystalline cellulose (Avicel PH 101 from the FMC company) | 94 mg |
| Lactose monohydrate (Lactose 200 from the Meggie company) | 30 mg |
| Highly dispersed silicon dioxide | 3 mg |
| Magnesium stearate | 3 mg |
| Total amount | 310 mg | were produced in the following way in a batch size of 2000 tablets:

All constituents were weighed out and screened on a Quadro Comil U10 screening machine using a screen size of 0.813 mm, mixed in a container mixer (Bohle LM 40) for 15 minutes±15 sec. at a rotational speed of 20±1 rpm, and compressed on a Korsch EKO eccentric press into tablets with a diameter of 10 mm having the contours of sugar-coated pills, a convex radius of 8 mm and a mean tablet weight of 310 mg.

The in vitro release was measured using the Ph. Eur. paddle method at 75 rpm in 900 ml of buffer pH 6.8 according to Ph. Eur. at 37° C. and with UV spectrometric detection, and is given in the following table.

| Time [min] | Released total amount of the active ingredient [%] |
|---|---|
| 0 | 0 |
| 30 | 22 |
| 240 | 69 |
| 480 | 88 |
| 720 | 96 |

Tablets according to Example 3 were stored for 3 months at 40° C. and 75% relative atmospheric humidity, for 9 months at 25° C. and 9 months at 30° C. (storage conditions according to ICH. The in vitro release was then redetermined using the Ph. Eur. paddle method at 75 rpm in 900 ml buffer pH 6.8 according to Ph. Eur. at 37° C. and with UV spectrometric detection, and is shown in the following table:

| | Storage Conditions | | |
|---|---|---|---|
| | 9 Months/25° C. | 9 Months/30° C. | 3 Months/40° C. 75% relative humidity |
| Time [min] | Released total amount of the active ingredient [%] | | |
| 0 | 0 | 0 | 0 |
| 30 | 21 | 21 | 21 |
| 240 | 73 | 72 | 77 |
| 480 | 93 | 92 | 94 |
| 720 | 100 | 99 | 100 |

Example 4

Matrix Tablets with the following composition per tablet

| | |
|---|---|
| (−)-(1R,2R)-1-dimethylamino-3-(3-methoxyphenyl)-2-methylpentan-3-ol; hydrochloride | 100 mg |
| Cellactose (Meggie) | 72.5 mg |
| Hydroxyethylcellulose (Natrosol 250 HX from the Hercules company) | 12.5 mg |
| Cutina HR (Henkel) | 150 mg |
| Talcum | 3 mg |
| Magnesium stearate | 2 mg |
| Total amount | 340 mg | were produced in the following way in a batch size of 200 tablets:

The active ingredient, Cellactose, Natrosol and Cutina were mixed, then heated in a drying cabinet to 80° C., and granulated in a Kenwood Chef kitchen mixer. The cooled granules were sieved through a 1 mm screen. After mixing with magnesium stearate and talcum, the granules were compressed in an EKO eccentric press (Korsch) into 6×15 mm large oblong tablets with a fracture notch.

The in vitro release was measured as in Example 1, and the results are shown in the following table:

| Time [min] | Released total amount of the active ingredient [%] |
|---|---|
| 0 | 0 |
| 30 | 10 |
| 240 | 53 |
| 480 | 69 |
| 720 | 80 |
| 900 | 98 |

Example 5

Pellets with the following composition

| | |
|---|---|
| (−)-(1R,2R)-1-dimethylamino-3-(3-methoxyphenyl)-2-methylpentan-3-ol; hydrochloride | 100 mg |
| Low-substituted hydroxypropylcellulose (L-HPC LH 31 from the Shinetsu company) | 75 mg |
| Aquacoat (aqueous ethylcellulose dispersion from the FMC company) (calculated as dry substance) | 20 mg |

-continued

| | |
|---|---|
| Microcrystalline cellulose (Avicel PH 101 from the FMC company) | 75 mg |
| Dibutyl sebacate (DBS) | 4 mg |
| Tween 80 | 0.4 mg |
| Total amount | 274.4 mg | were produced in the following way:

The active ingredient, Avicel and L-HPC were mixed in a planetary mixer (Kenwood K mixer) for 10 minutes and then granulated with water. The moist granules were extruded in a Nica extruder with a 0.8×0.8 mm matrix and then rounded for 10 minutes in a Nica spheroniser at 500 rpm (load 1 kg). The pellets were dried overnight in a drying cabinet at 50° C. and then graded in screening fractions. Pellets of size 0.6-1.0 mm (yield ca. 95%) were coated in the WSG (smooth GPCG1 with Wurster insert) at feed air temperatures of 60° C. (product temperature 40° C.) with an aqueous dispersion of Aquacoat and DBS (20%, calculated in terms of Aquacoat solids content), so as to produce a weight increase of 9.8% (referred to the initial weight). The dispersion was produced according to the manufacturer's data (FA, FMC), and the DBS together with Tween 80 were homogenised in part of the water and then added to the diluted Aquacoat dispersion. The ready-for-use dispersion had a solids content of 20 wt. % and was stirred for at least 3 hours. The coated pellets were dried in the WSG and heat treated in the drying cabinet (2 hours at 60° C.). The release was determined similarly to Example 1, but according to the basket method at 100 rpm.

| Time [min] | Released total amount of the active ingredient [%] |
|---|---|
| 0 | 0 |
| 30 | 2 |
| 240 | 29 |
| 480 | 67 |
| 720 | 78 |
| 900 | 89 |
| 1080 | 101 |

Example 6

List of Tested Substances

A list of the compounds tested for their effectiveness is given below:

| Name | Cmpd. No. |
|---|---|
| (2RS,3RS)-1-dimethylamino-3-(3-methoxyphenyl)-2-methylpentan-3-ol; hydrochloride | 1 |
| (+)-(2R,3R)-1-dimethylamino-3-(3-methoxyphenyl)-2-methylpentan-3-ol; hydrochloride | 2 |
| (−)-(2S,3S)-1-dimethylamino-3-(3-methoxyphenyl)-2-methylpentan-3-ol; hydrochloride | 21 |

Example 8

Cystometry Test System on Conscious Fresh Rats

Cystometry investigations were carried out on fresh female Sprague-Dawley rats according to the method of Ishizuka et al. ((1997), Naunyn-Schmiedeberg's Arch. Pharmacol. 355: 787-793). Three days after implantation of bladder and venous catheters the animals were investigated in the conscious state while freely moving. The bladder catheter was connected to a pressure gauge and an injection pump. The animals were placed in metabolic cages that enabled the volume of urine to be measured. Physiological saline solution was infused (10 ml/hour) into the emptied bladder and the bladder pressure and volume of urine were continuously recorded. After a stabilisation phase a 20-minute phase was recorded that was characterised by normal, reproducible micturition cycles. The following parameters among others were measured:

threshold pressure TP, bladder pressure immediately before micturition, bladder capacity BC, residual volume after prior micturition plus volume of infused solution during the filling phase, intercontraction interval ICI, i.e. the time interval between consecutive micturition.

An increase in the threshold pressure (TP) indicates an important therapeutic effect in one of the medical conditions covered by the invention. Also, the intercontraction interval (ICI) is an important parameter for measuring the physiological effectiveness of a substance in the treatment of urinary incontinence, as is the bladder capacity (BC). In this connection, on account of the widely differing causes of the symptoms of these disease patterns it is not necessary to influence positively all three parameters in order for a medicament to be effective. It is therefore perfectly adequate if a positive effect is demonstrated in only one of these parameters in order for the medicament to be of use in urinary incontinence or increased urinary urgency.

After recording three reproducible micturition cycles to provide a baseline value, the test substances (1 (1.0 mg/kg), 2 (0.1; 0.3 and 0.5 mg/kg) and 21 (0.5 mg/kg), in a vehicle comprising 0.9% NaCl were applied intravenously and the effect on the cystometric parameters was recorded at 90 to 120 minutes. In the effect maximum the mean value of 3 micturition cycles was determined and recorded as a percentage change compared to the baseline value (Table 1).

TABLE 1

Influencing of the cystometric parameters by the test substances (change compared to the baseline value(%));
n corresponds to the number of experimental animals; significance
(Student T Test): *p < 0.05; p < 0.01; *p < 0.001.

| Compound: (Concentration) | TP Threshold Pressure | BC Bladder Capacity | ICI Inter-Contraction Interval |
|---|---|---|---|
| 1 | | | |
| 1.0 mg/kg iv (n = 9) | +94%** | +31%*** | +42% |
| 2 | | | |
| 0.1 mg/kg iv (n = 5) | +28.5%** | +7.8% | +15.6% |
| 0.3 mg/kg iv (n = 8) | +122%** | +33%* | +28%* |

TABLE 1-continued

Influencing of the cystometric parameters by the test substances (change compared to the baseline value(%)); n corresponds to the number of experimental animals; significance (Student T Test): *p < 0.05; p < 0.01; *p < 0.001.

| Compound: (Concentration) | TP Threshold Pressure | BC Bladder Capacity | ICI Inter-Contraction Interval |
|---|---|---|---|
| 0.5 mg/kg iv (n = 9) 21 | +77.5%** | +20.6%* | +28.6%** |
| 0.5 mg/kg iv (n = 8) | −1.1% | +3% | +10% |

The investigated substances exhibit a positive effect on the bladder regulation and are therefore suitable for treating urinary incontinence. It was found inter alia that, of the enantiomers of the racemic compound 1, the (+) enantiomer (compound 2) is very effective (and thus is a particularly preferred compound of the invention), while the (−) enantiomer (compound 21) does not exhibit such a marked effect.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A delayed release pharmaceutical formulation containing:
   1-dimethylamino-3-(3-methoxyphenyl)-2-methylpentan-3-ol or a pharmaceutically acceptable salt thereof in a release-delaying matrix, said matrix comprising from 1 to 80 wt. % of at least one pharmaceutically acceptable, matrix-forming, polymer, and said formulation exhibiting the following in vitro release rates relative to 100% of the 1-dimethylamino-3-(3-methoxyphenyl)-2-methylpentan-3-ol initially contained therein measured using the Ph. Eur. paddle method at 75 rpm in a buffer at a pH value of 6.8 at 37° C. and with UV spectrometric detection:
   3-35 wt. % released after 0.5 hour,
   5-50 wt. % released after 1 hour,
   10-75 wt. % released after 2 hours,
   15-82 wt. % released after 3 hours,
   30-97 wt. % released after 6 hours,
   more than 50 wt. % released after 12 hours,
   more than 70 wt. % released after 18 hours, and
   more than 80 wt. % released after 24 hours.

2. A delayed release pharmaceutical formulation containing 1-dimethylamino-3-(3-methoxyphenyl)-2-methylpentan-3-ol or a pharmaceutically acceptable salt thereof in a release-delaying matrix, said matrix comprising from 1 to 80 wt. % of at least one pharmaceutically acceptable, matrix-forming polymer, wherein said polymer comprises a cellulose ether or cellulose ester that has a viscosity of 3000 to 150,000 mPas in a 2 wt. % aqueous solution at 20° C.

3. A pharmaceutical formulation according to claim 1, wherein said matrix comprises a cellulose ether or cellulose ester that has a viscosity of 10,000 to 150,000 mPas in a 2 wt. % solution at 20° C.

4. A pharmaceutical formulation according to claim 3, wherein said matrix comprises a cellulose ether or cellulose ester that has a viscosity of 50,000 to 150,000 mPas in a 2 wt. % solution at 20° C.

5. A pharmaceutical formulation according to claim 1, wherein said matrix comprises at least one substance selected from the group consisting of hydroxypropylmethylcelluloses (HPMC), hydroxyethylcelluloses, hydroxypropylcelluloses (HPC), methylcelluloses, ethylcelluloses and carboxymethylcelluloses.

6. A pharmaceutical formulation according to claim 5, wherein said matrix comprises at least one substance selected from the group consisting of hydroxypropylmethylcelluloses, hydroxyethylcelluloses and hydroxypropylcelluloses.

7. A pharmaceutical formulation according to claim 1, wherein said formulation contains from 0.5 to 85 wt. % of said 1 dimethylamino-3-(3-methoxyphenyl)-2-methylpentan-3-ol or pharmaceutically acceptable salt thereof and from 8 to 40 wt. % of the at least one pharmaceutically acceptable matrix-forming polymer.

8. A pharmaceutical formulation according to claim 7, containing from 3 to 70 wt. % of said 1-dimethylamino-3-(3-methoxyphenyl)-2-methylpentan-3-ol or pharmaceutically acceptable salt thereof, and from 10 to 35 wt. % of the at least one pharmaceutically acceptable matrix-forming polymer.

9. A pharmaceutical formulation according to claim 8, containing from 8 to 66 wt. % of said 1-dimethylamino-3-(3-methoxyphenyl)-2-methylpentan-3-ol or pharmaceutically acceptable salt thereof, and from 10 to 30 wt. % of the at least one pharmaceutically acceptable matrix-forming polymer.

10. A pharmaceutical formulation according to claim 1, wherein said formulation produces a peak plasma level of said 1 dimethylamino-3-(3-methoxyphenyl)-2-methylpentan-3-ol or pharmaceutically acceptable salt thereof in vivo from 2 to 10 hours after administration.

11. A pharmaceutical formulation according to claim 10, wherein said peak plasma level is produced from 3.5 to 6 hours after administration.

12. A pharmaceutical formulation according to claim 1, comprising (+)-(2R,3R)-1-dimethylamino-3-(3-methoxyphenyl)-2-methylpentan-3-ol or a pharmaceutically acceptable salt thereof.

13. A pharmaceutical formulation according to claim 1, in the form of a tablet for twice daily oral administration.

14. A delayed release pharmaceutical formulation containing 1-dimethylamino-3-(3-methoxyphenyl)-2-methylpentan-3-ol or a pharmaceutically acceptable salt thereof in a release-delaying matrix, said matrix comprising from 1 to 80 wt. % of at least one pharmaceutically acceptable, matrix-forming, polymer, wherein said polymer comprises a cellulose ether or cellulose ester that has a viscosity of 3000 to 150,000 mPas in a 2 wt. % aqueous solution at 20° C.

15. A pharmaceutical formulation according to claim 14, wherein said matrix comprises a cellulose ether or cellulose ester that has a viscosity of 10,000 to 150,000 mPas in a 2 wt. % solution at 20° C.

16. A pharmaceutical formulation according to claim 15, wherein said matrix comprises a cellulose ether or cellulose ester that has a viscosity of 50,000 to 150,000 mPas in a 2 wt. % solution at 20° C.

17. A pharmaceutical formulation according to claim 14, wherein said matrix comprises at least one substance selected from the group consisting of hydroxypropylmethylcelluloses (HPMC), hydroxyethylcelluloses, hydroxypropylcelluloses (HPC), methylcelluloses, ethylcelluloses and carboxymethylcelluloses.

18. A pharmaceutical formulation according to claim 17, wherein said matrix comprises at least one substance selected from the group consisting of hydroxypropylmethylcelluloses, hydroxyethylcelluloses and hydroxypropylcelluloses.

19. A pharmaceutical formulation according to claim 14, wherein said formulation contains from 0.5 to 85 wt. % of said 1 dimethylamino-3-(3-methoxyphenyl)-2-methylpentan-3-ol or pharmaceutically acceptable salt thereof and from 8 to 40 wt. % of the at least one pharmaceutically acceptable matrix-forming polymer.

20. A pharmaceutical formulation according to claim 19, containing from 3 to 70 wt. % of said 1-dimethylamino-3-(3-methoxyphenyl)-2-methylpentan-3-ol or pharmaceutically acceptable salt thereof, and from 10 to 35 wt. % of the at least one pharmaceutically acceptable matrix-forming polymer.

21. A pharmaceutical formulation according to claim 20, containing from 8 to 66 wt. % of said 1-dimethylamino-3-(3-methoxyphenyl)-2-methylpentan-3-ol or pharmaceutically acceptable salt thereof, and from 10 to 30 wt. % of the at least one pharmaceutically acceptable matrix-forming polymer.

22. A pharmaceutical formulation according to claim 14, wherein said formulation produces a peak plasma level of said 1 dimethylamino-3-(3-methoxyphenyl)-2-methylpentan-3-ol or pharmaceutically acceptable salt thereof in vivo from 2 to 10 hours after administration.

23. A pharmaceutical formulation according to claim 22, wherein said peak plasma level is produced from 3.5 to 6 hours after administration.

24. A pharmaceutical formulation according to claim 14, comprising (+)-(2R,3R)-1-dimethylamino-3-(3-methoxyphenyl)-2-methylpentan-3-ol or a pharmaceutically acceptable salt thereof.

25. A pharmaceutical formulation according to claim 14, in the form of a tablet for twice daily oral administration.

26. A method of treating increased urinary urgency or urinary incontinence in a patient in need thereof, said method comprising administering to said patient a pharmaceutically effective amount of a delayed release pharmaceutical formulation according to claim 1.

27. A method of treating pain in a patient in need thereof, said method comprising administering to said patient a pharmaceutically effective amount of a delayed release pharmaceutical formulation according to claim 1.

28. A method according to claim 27, wherein said pain is selected from the group consisting of chronic pain, visceral pain, neuropathic pain, acute pain and inflammation pain.

29. A method of treating increased urinary urgency or urinary incontinence in a patient in need thereof, said method comprising administering to said patient a pharmaceutically effective amount of a delayed release pharmaceutical formulation according to claim 14.

30. A method of treating pain in a patient in need thereof, said method comprising administering to said patient a pharmaceutically effective amount of a delayed release pharmaceutical formulation according to claim 14.

31. A method according to claim 30, wherein said pain is selected from the group consisting of chronic pain, visceral pain, neuropathic pain, acute pain and inflammation pain.

32. A pharmaceutical formulation according to claim 1, wherein said polymer is hydrophilic.

33. A pharmaceutical formulation according to claim 1, wherein said polymer is hydrophobic.

* * * * *